United States Patent
Patel et al.

(10) Patent No.: US 7,750,201 B2
(45) Date of Patent: *Jul. 6, 2010

(54) WOUND DRESSINGS WITH ANTI-MICROBIAL AND CHELATING AGENTS

(75) Inventors: Harish A. Patel, Norfolk, MA (US); Hansen P. Swaniker, Bristol, RI (US); David G. Heagle, Franklin, MA (US); Kate Ward, Marshfield, MA (US); Alain Tranchemontagne, Warwick, RI (US); E. David Fink, Franklin, MA (US); Ronald F. Vitaris, Worcester, MA (US); Chirag B. Shah, North Attleboro, MA (US); Sharon A. Mulligan, Bristol, RI (US); Brian Dowd, Dedham, MA (US); Scott Orr, Franklin, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 207 days.

This patent is subject to a terminal disclaimer.

(21) Appl. No.: 11/783,667

(22) Filed: Apr. 11, 2007

(65) Prior Publication Data

US 2007/0255192 A1 Nov. 1, 2007

Related U.S. Application Data

(60) Provisional application No. 60/790,813, filed on Apr. 11, 2006.

(51) Int. Cl.
*A61F 13/00* (2006.01)
*A61L 15/16* (2006.01)

(52) U.S. Cl. .................. 602/48; 602/43; 604/304; 424/443; 424/446; 424/447

(58) Field of Classification Search .................. 602/48, 602/54, 43, 44, 45, 55, 358; 604/367, 310, 604/312, 383, 368, 378, 304–308, 358, 904, 604/11; 424/443, 444, 445, 446, 447, 448, 424/449

See application file for complete search history.

(56) References Cited

U.S. PATENT DOCUMENTS

| | | | |
|---|---|---|---|
| 2,838,045 A | 6/1958 | Ryzmar | |
| 2,934,066 A | 4/1960 | Stowasser | |
| 3,920,020 A | 11/1975 | Kraskin | |
| 4,211,227 A * | 7/1980 | Anderson et al. | 604/366 |
| 4,587,266 A | 5/1986 | Verdicchio | |
| 4,643,180 A | 2/1987 | Feld et al. | |
| 4,857,334 A | 8/1989 | Korol et al. | |
| 5,059,189 A | 10/1991 | Cilento et al. | |
| 5,362,754 A | 11/1994 | Raad et al. | |
| 5,449,658 A | 9/1995 | Unhoch et al. | |

(Continued)

FOREIGN PATENT DOCUMENTS

WO   WO 02/38097   *   5/2002

(Continued)

*Primary Examiner*—Patricia M Bianco
*Assistant Examiner*—Ophelia Hawthorne
(74) *Attorney, Agent, or Firm*—Elizabeth A. O'Brien, Esq.

(57) ABSTRACT

A wound dressing includes one or more layers containing a first anti-microbial agent and at least one of: a chelating agent, and a second anti-microbial agent.

30 Claims, 2 Drawing Sheets

U.S. PATENT DOCUMENTS

| | | | |
|---|---|---|---|
| 5,688,516 A | 11/1997 | Raad et al. | |
| 5,782,787 A | 7/1998 | Webster | |
| 5,817,325 A | 10/1998 | Sawan et al. | |
| 5,830,526 A | 11/1998 | Wilson et al. | |
| 5,856,248 A | 1/1999 | Weinberg | |
| 5,931,800 A | 8/1999 | Rasmussen et al. | |
| 6,042,877 A | 3/2000 | Lyon et al. | |
| 6,114,594 A * | 9/2000 | Barikosky | 604/367 |
| 6,160,196 A | 12/2000 | Knieler et al. | |
| 6,180,132 B1 | 1/2001 | Huang et al. | |
| 6,187,290 B1 | 2/2001 | Gilchrist et al. | |
| 6,187,768 B1 | 2/2001 | Welle et al. | |
| 6,239,048 B1 | 5/2001 | Wilson et al. | |
| 6,706,279 B1 | 3/2004 | Hazzi | |
| 6,762,339 B1 * | 7/2004 | Klun et al. | 602/58 |
| 7,005,556 B1 | 2/2006 | Becker et al. | |
| 7,270,721 B2 * | 9/2007 | Hilfenhaus et al. | 156/60 |
| 2002/0091074 A1 | 7/2002 | Wooley et al. | |
| 2002/0098208 A1 | 7/2002 | Wooley et al. | |
| 2003/0176827 A1 * | 9/2003 | Chandra et al. | 602/48 |
| 2003/0216479 A1 | 11/2003 | Huang et al. | |
| 2004/0015115 A1 * | 1/2004 | Sinyagin | 602/42 |
| 2004/0047763 A1 | 3/2004 | Kite et al. | |
| 2004/0082925 A1 * | 4/2004 | Patel | 604/289 |
| 2004/0142829 A1 | 7/2004 | Tsao et al. | |
| 2004/0151765 A1 | 8/2004 | Ritchie et al. | |
| 2004/0241216 A1 | 12/2004 | Klun et al. | |
| 2005/0261148 A1 | 11/2005 | Xia et al. | |
| 2006/0035039 A1 | 2/2006 | Ylitalo et al. | |

FOREIGN PATENT DOCUMENTS

WO    WO 2007084533 A2 *    7/2007

* cited by examiner

WOUND DRESSINGS WITH ANTI-MICROBIAL AND CHELATING AGENTS

The present nonprovisional application claims priority, pursuant to 35 U.S.C. §119, to provisional application Ser. No. 60/790,813 filed Apr. 11, 2006, the entire content of which is incorporated herein by reference.

BACKGROUND

In the discussion of the state of the art that follows, reference is made to certain structures and/or methods. However, the following references should not be construed as an admission that these structures and/or methods constitute prior art. Applicant expressly reserves the right to demonstrate that such structures and/or methods do not qualify as prior art.

A variety of wound dressings have been suggested. However, such wound dressings possess various deficiencies and shortcomings.

For example, a number of wound dressings have been proposed which include various anti-microbial agents. Logically, an increase in the amount of anti-microbial agent contained in the wound dressing would result in an increased effectiveness in combating and/or preventing infection. However, certain popular anti-microbial agents, such as chlorohexidine gluconate (CHG) can have an irritating effect on the skin, especially when higher levels or concentrations of CHG are applied.

Thus, a need exists in the art for wound dressings which have increased effectiveness in combating and/or preventing infection, but which do not possess disadvantages, such as increased skin irritation.

SUMMARY

According to one optional aspect of the present invention, increased control of bioburdens is provided, without resorting to increased concentrations of anti-microbial agents, such as PHMB. According to a further optional aspect of the present invention, the wound dressing is provided which reduces the risk of infection, or facilitates the control of an existing infection, without change to the existing wound care protocol. According to yet a further optional aspect of the present invention, there is provided a wound dressing which will effectively increase the spectrum of activity of the anti-microbial agent contained therein. According to another optional aspect of the present invention, a wound dressing is provided which provides targeted and/or controlled delivery of an anti-microbial agent and/or additional additives contained in the wound dressing to the wound site.

A wound dressing of the present invention can comprise one or more layers containing a first anti-microbial agent and at least one of: a chelating agent, and a second anti-microbial agent.

A wound dressing according to the present invention can alternatively comprise at least a first layer, a second layer and a third layer, wherein at least one of the first, second and third layers contains an anti-microbial agent and/or a chelating agent.

A wound dressing according to a further alternative embodiment comprises at least a first layer, a second layer and a third layer, wherein at least the one of the first, second and third layers contains an anti-microbial agent, and at least another of the first, second and third layers contains a chelating agent.

According to the present invention, there can also be provided a wound dressing comprising: a first inner layer containing an anti-microbial agent; and second and third outer layers adjacent to the first layer, the second and third layers containing a chelating agent.

A wound dressing formed according to another alternative embodiment can comprise a first inner layer containing a chelating agent; and second and third outer layers adjacent to the first layer, the second and third layers containing an anti-microbial agent.

The present invention also contemplates a wound dressing comprising: a first inner layer; and second and third outer layers, wherein each of the first, second and third layers contain an anti-microbial agent and a chelating agent.

A wound dressing formed according to yet another alternative configuration can comprise one or more layers formed from a combination of fibers, the combination of fibers comprising at least a first fiber and a second fiber, wherein the first fiber is treated with at least a first anti-microbial agent, and the second fiber is treated with at least a second anti-microbial agent.

A wound dressing of the present invention may further comprise one or more layers formed from a homogenous blend of fibers, the combination of fibers comprising at least a first fiber and a second fiber, wherein the first fiber is treated with at least a first anti-microbial agent, and a second fiber is treated with at least a second anti-microbial agent.

According to the present invention, there can also be provided a wound dressing comprising one or more layers formed from a combination of fibers, the combination of fibers comprising at least a first fiber and a second fiber, wherein the first fiber is treated with at least a first anti-microbial agent, and the second fiber is treated with at least a second anti-microbial agent, and wherein the amount of first fiber present in the wound dressing is different than the amount of second fiber present in the wound dressing.

According to yet another alternative configuration, the present invention provides a wound dressing comprising one or more layers formed from a combination of fibers, the combination of fibers comprising at least a first fiber and a second fiber, wherein the first fiber is treated with at least a first anti-microbial agent, and the second fiber is treated with at least a second anti-microbial agent, and wherein the density of either the first fiber, second fiber, or both, vary along a concentration gradient.

A wound dressing formed according to yet another embodiment can comprise a first layer disposed on a first side of the dressing adapted to be applied to the wound surface, the first layer containing at least one anti-microbial agent; and a second layer adjacent to the first layer, and disposed on a side thereof opposite the first side of the dressing, the second layer containing a cell-signaling agent.

As used herein "containing" or "contains" is broadly construed to mean that the one or more layers themselves and/or the material(s) making up the layers are impregnated with, and/or have coatings/treatments of other material(s)/agent(s) applied thereto. The impregnation and/or coatings/treatments may be applied to all or a portion of the layers or the material (s) forming the layers. Finally, the term encompasses all methods or techniques of impregnation and/or coatings/treatments, regardless of the state of the material(s)/agent(s) being applied thereto (e.g., solid, liquid, gas, plasma, etc.). The added material(s)/agent(s) can be applied during manufacture, or subsequent thereto (e.g., by the user/consumer prior to application of the one or more layers to the wound site).

DETAILED DESCRIPTION

Figure 1:
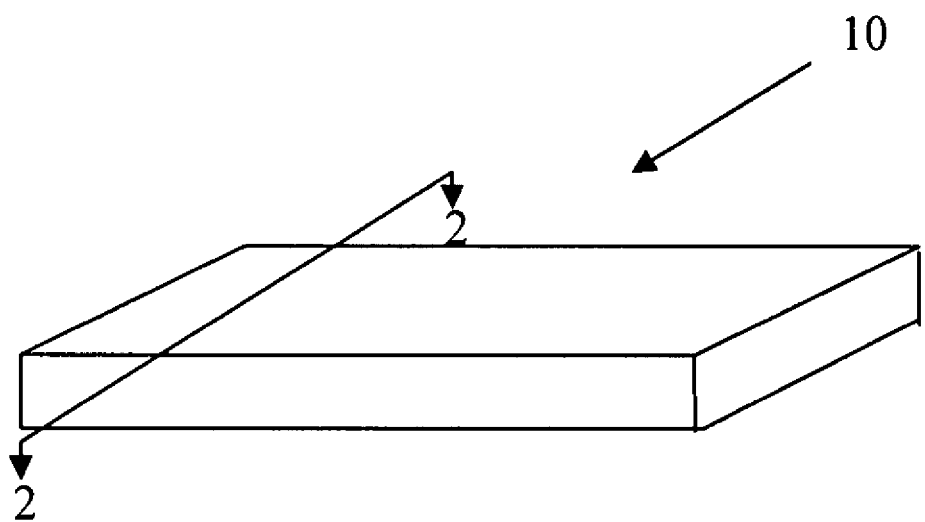
FIG. 1 is a schematic illustration of an exemplary embodiment of an anti-microbial wound dressing of the present invention.
Figure 2:
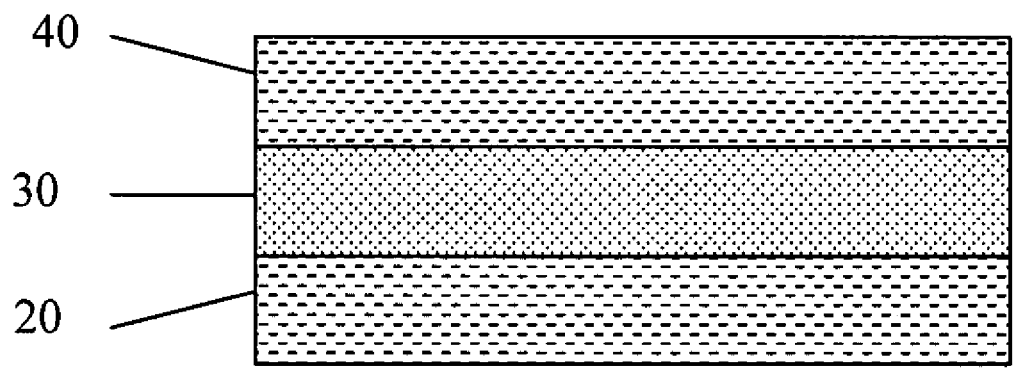
FIG. 2 is a schematic cross-sectional illustration, taken along lines 2-2 of FIG. 1 of alternative embodiments of an anti-microbial wound dressing of the present invention.
Figure 3:
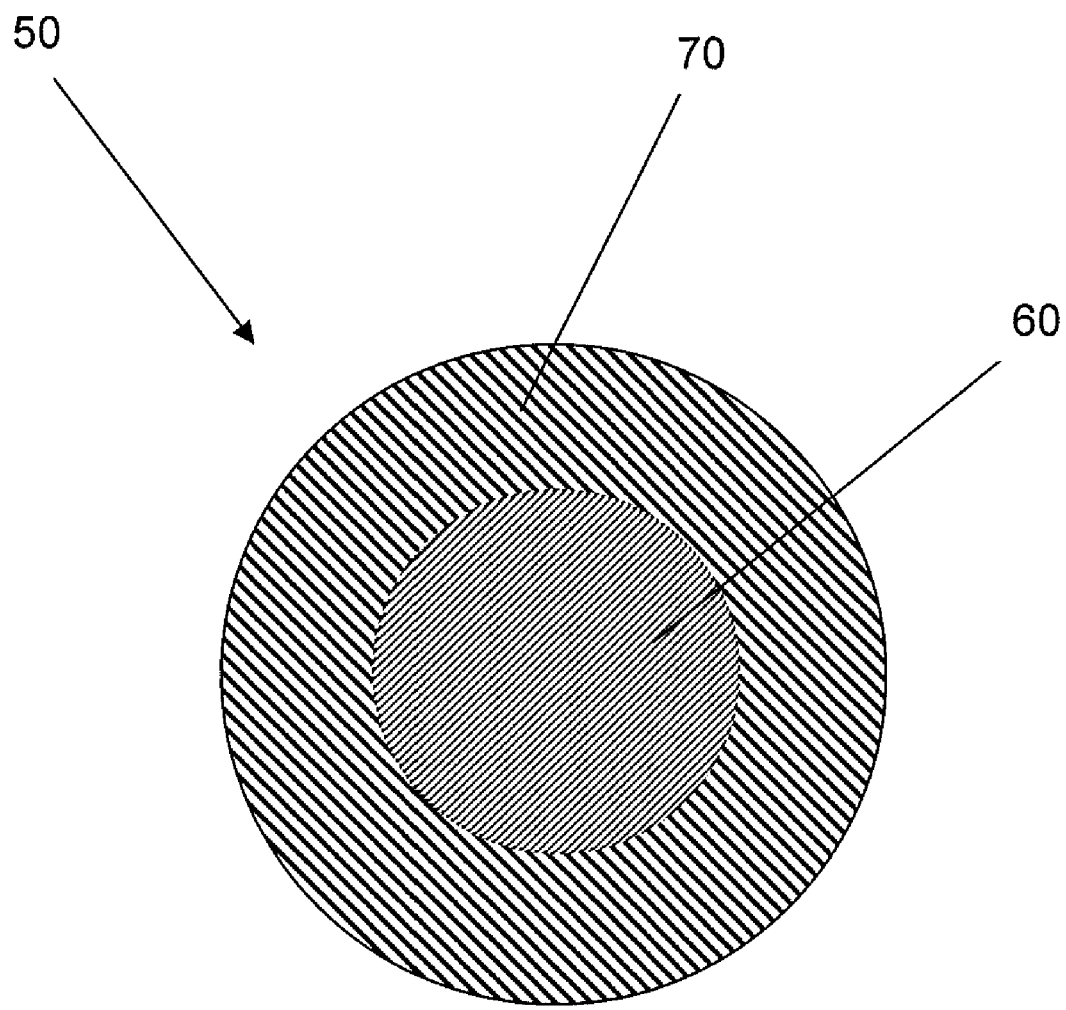
FIG. 3 is a schematic cross-sectional view of a fiber formed according to certain embodiments of the present invention.

FIGS. 1-3 may be referred to in order to facilitate the following discussion. In broader aspects, the present invention provides a wound dressing comprising one or more layers containing a first anti-microbial agent and at least one of: a chelating agent, and a second anti-microbial agent.

A wound dressing formed according to the principles of the present invention can be generally formed from one or more discrete layers (e.g., 20, 30, 40). Each of the one or more layers can be formed from any suitable material and/or construction. For example, the one or more layers can be formed from a fibrous, film-like, or foam material. With respect to fibrous materials, they can be woven or nonwoven materials. The fibers can be selected from natural fibers, synthetic fibers, and combinations of the two. By way of non-limiting example, suitable materials which can be utilized to form the one or more layers of the present invention include: cellulose, alginates, cotton, Rayon, Nylon, acrylic, polyester, polyurethane, polyurethane foam, and combinations thereof.

A wound dressing of the present invention may include one or more anti-microbial agents. A number of alternative anti-microbial agents are possible. Suitable anti-microbial agents include, but are not limited to, a chlorhexidine, a chlorhexadine salt, a triclosan, a polymoxin, a tetracycline, an amino glycoside (e.g., gentamicin or Tobramycin™), a rifampicin, a bacitracin, an erythromycin, a neomycin, a chloramphenicol, a miconazole, a quinolone, a penicillin, a nonoxynol 9, a fusidic acid, a cephalosporin, a mupirocin, a metronidazole, a secropin, a protegrin, a bacteriolcin, a defensin, a nitrofurazone, a mafenide, a acyclovir, a vanocmycin, a clindamycin, a lincomycin, a sulfonamide, a norfloxacin, a pefloxacin, a nalidizic acid, an oxalic acid, an enoxacin acid, a ciprofloxacin, a biguanide, combinations thereof and the like. In certain embodiments the anti-microbial agent comprises polyhexamethylene biguanide (PHMB) and/or derivatives thereof.

A wound dressing of the present invention may further include a chelating agent. Any suitable chelating agent may be utilized. By way of non-limiting example, chelating agents such as ethylenediaminetetraacetic acid (EDTA), variations of EDTA such as, for example, disodium EDTA or tetrasodium EDTA, combinations thereof and the like, are contemplated. Chelating agents can heighten the susceptibility of bacteria and other organisms to the antiseptic effects of the anti-microbial agent, thereby rendering the wound dressing more effective in combating and/or preventing infection, without the necessity of increasing the levels of anti-microbial agent contained therein. This aspect of the present invention advantageously avoids problems caused by the irritating effects of certain anti-microbial agents, such as CHG, especially when applied to the skin that higher concentration levels.

As an additional component, or as a substitute for one or more of the above-mentioned anti-microbial agents and/or chelating agents, a wound dressing formed according to the principles of the present invention may include one or more additional anti-microbial agents. By way of non-limiting example, suitable additional anti-microbial agents include, but are not limited to: polyethylene hexamethylene biguanide (PEHMB), silver, zinc, copper, and combinations thereof.

Exemplary wound dressings can, of course, include additional active ingredients or agents such as, for example, a therapeutic agent, an organoleptic agent, a growth factor, an analgesic, a tissue scaffolding agent, a haemostatic agent, a protein inhibitor, collagen, enzymes, an anti-thrombogenic agent, an anesthetic, an anti-inflammatory agent, an anticancer agent, a vasodilation substance, a wound healing agent, an angiogenic agent, an angiostatic agent, an immune boosting agent, a skin sealing agent, an agent to induce directional bacterial growth, an agent to impart bacteriacidal or bacteriostatic activity, an electron transfer agent to destabilize or destroy the metabolic action of microbes and/or biofilm formation, combinations thereof and the like. Release of active agents may be triggered by a variety of means, such as, for example, an electric field or signal, temperature, time, pressure, moisture, light (e.g., ultra-violet light), ultrasound energy, sonication, combinations thereof and the like.

According to the present invention, any of the above-mentioned anti-microbial, chelating, or additional active agents may be combined directly with the material forming the one or more layers of the wound dressing. Alternatively, any of the above-mentioned agents may be contained, and subsequently released, by a delivery agent. Any suitable delivery agent can be utilized. By way of non-limiting example, suitable delivery agents include: a hydrogel, phosphate glass, powdered starch, or a starch film.

Wound dressings formed according to the present invention can be provided in numerous configurations, having a number of different combinations of features. In the discussion that follows, any of the above-mentioned agents or additives can be included in the illustrative configurations discussed below, unless otherwise indicated.

According to one possible configuration of the present invention, a wound dressing is provided which comprises one or more layers containing at least one anti-microbial agent and at least one chelating agent. According to one optional modification, all layers of the wound dressing may contain a combination of anti-microbial agent and chelating agent.

According to another alternative modification of the above multi-layer configuration, the anti-microbial agent and the chelating agent can be separately contained in different layers of the wound dressing. Thus, for example, a wound dressing can be formed with at least three distinct layers; an inner layer (e.g., 30), and two adjacent outer layers (e.g., 20, 40). The anti-microbial agent can be contained in the inner layer, which is not in direct contact with the skin or wound, and the chelating agent can be provided in one or more of the outer layers. The inner layer may be substantially hydrophilic, while one or more of the outer layers may be substantially hydrophobic. Although an anti-microbial agent, and possibly also a chelating agent, may be released from the inner layer material of the fabric, the anti-microbial treatment of the fabric principally allows the dressing to function as a barrier to contamination of the wound from sources outside the wound. In addition, due to the absorbent characteristics of the dressing, microbes absorbed within the inner layer are prevented from escaping through the dressing. The term "substantially hydrophilic" describes the function of the inner layer material. It also distinguishes the inner layer material over the function of the "substantially hydrophobic" outer layer material, which provides an anti-microbial barrier property and attenuates or reduces the release of anti-microbial agent away from the dressing. The improved retention of anti-microbial agent within the inner layer also lowers the bioburden, i.e., the growth and number of cells, within the dressing during use. As an optional modification of the above, the chelating agent can be provided in the inner layer, and the anti-microbial agent provided in one or more of the adjacent outer layers.

When the wound dressings of the present invention are formed from fibrous materials, the wound dressing can be provided with a combination of anti-microbial agents and/or anti-microbial agents and chelating agents, by treating different fibers with different agents, then combining the fibers in a desired manner to provide the wound dressing with a particular anti-microbial effect or behavior. Thus, for example, the wound dressing may comprise one or more layers formed as a homogenous blend of the above-described treated fibers. Alternatively, the wound dressing can be formed from one or more layers composed of fibers which vary in density and anti-microbial treatment levels. By way of nonlimiting example, suitable fibers such as cellulose, Rayon, etc. can be treated and bound to PHMB in various concentrations. Other fibers, such as Nylon, polypropylene or amorphous polyester, can be compounded with a silver anti-microbial agent in the base resin, and spun into fiber form. The amount of silver added to the base resin can vary between about 0.5-40% by weight. As an alternative, the fiber can be constructed from two basic components. Specifically, as illustrated in FIG. 3 the fiber 50 can comprise an inner core 60 and an outer sheath 70 which contains a relatively higher amount of silver anti-microbial agent. According to this alternative, the outer sheath 70 can comprise up to 70% by weight of the silver anti-microbial agent, while the inner core 60 which provides structural integrity to the fiber, has a lower amount of silver anti-microbial agent, on the order of less than 20% by weight. According to this combination of anti-microbial ingredients, the effects of PHMB would be quicker, and the effects of the silver anti-microbial agent, more prolonged. It is contemplated that other combinations of anti-microbials are possible. By way of nonlimiting example, other metal-based anti-microbial agents, such as those based on zinc or copper, could be utilized instead of the silver anti-microbial agent. A chelating agent, such as EDTA, can be added to the above-mentioned combination of anti-microbial agents in order to improve the efficacy thereof.

According to an alternative configuration, the wound dressing is formed from a material, such as a polyurethane foam, which is then combined with a number of anti-microbial agents, and or a chelating agent, thereby providing a synergistic benefit.

According to a further alternative construction, the wound dressing is formed from a plurality of different layers and materials containing agents to enhance performance. A cell-signaling agent or material can be provided in the dressing between the wound bed and another dressing layer which is treated with one or more anti-microbial agents. According to this construction, bacteria would need to cross the anti-microbial agent to reach the signaling mechanism. A cell signaling mechanism is a means of communicating with the cell by electrical, chemical or biologic means that encourages cell growth or movement or receptive action in the direction of that signal. That signal may also deactivate the bacterial cells defense mechanisms. According to this construction, bacterial growth is promoted in a preferred manner (i.e., away from the wound bed) which leads to an increased efficacy of the wound dressing. One exemplary cell signaling mechanism is Nitric Oxide (NO), which diffuses and bind with the cell membrane to produce the desired effect at the wound site. A steroid molecule is another example of a possible cell-signaling substance All numbers expressing quantities of ingredients, constituents, reaction conditions, and so forth used in the specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, may inherently contain certain errors as evident from the standard deviation found in their respective measurement techniques.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

We claim:

1. A wound dressing comprising one or more layers, each layer comprising a combination of fibers, the combination of fibers comprising at least a first fiber and a second fiber, wherein the first fiber is treated with at least a first anti-microbial agent comprising PHMB, and the second fiber is treated with at least a second anti-microbial agent.

2. The wound dressing of claim 1, wherein the second fiber is compounded with at least one of: silver, zinc or copper.

3. The wound dressing of claim 2, wherein the fiber is compounded with about, in percent by weight, 0.1% to about 40% silver.

4. The wound dressing of claim 2, wherein the fiber comprises a core and a surrounding sheath, wherein the core is compounded with a first amount of silver, and the surrounding sheath is compounded with a second amount of silver, the second amount being greater than the first amount.

5. The wound dressing of claim 4, wherein the first amount is less than about 20% by weight, and the second amount is less than about 70% by weight.

6. The wound dressing of claim 1, wherein the combination of fibers comprises a homogenous blend of fibers.

7. The wound dressing of claim 1, wherein the amount of first fiber present in the wound dressing is different than the amount of second fiber present in the wound dressing.

8. The wound dressing of clam 1, wherein the density of either the first fiber, second fiber, or both, vary along a concentration gradient.

9. A wound dressing comprising a first layer, a second layer and a third layer, wherein at least one of the first, second and third layers contains an anti-microbial agent, and at least another of the first, second and third layers contains a chelating agent and wherein the anti-microbial agent and the chelating agent are separately contained in different layers of the wound dressing.

10. The wound dressing of claim 9, wherein the first inner layer is substantially hydrophilic, and the second and third outer layers are substantially hydrophobic.

11. The wound dressing of claim 10, wherein the second and third outer layers comprise a hydrophilic finish.

12. The wound dressing of claim 9, further comprising a delivery agent for containing and releasing at least one of the anti-microbial agent and the chelating agent.

13. The wound dressing of claim 12, wherein the delivery agent comprises one or more of: a hydrogel, phosphate glass, powdered starch, or a starch film.

14. The wound dressing of claim 9, comprising:
a first inner layer containing the first anti-microbial agent; and
second and third outer layers adjacent to the first layer, the second and third layers containing the chelating agent.

15. The wound dressing of claim 9, comprising:
a first inner layer containing the chelating agent; and
second and third outer layers adjacent to the first layer, the second and third layers containing the first anti-microbial agent.

16. The wound dressing of claim 9, wherein the one or more layers are formed, at least in part, by one or more of: natural fibers, synthetic fibers, cellulose, cotton, Rayon, Nylon, acrylic, polyester, polyurethane, polyurethane foam, hydrogels, starch, a starch film, a biodegradable material, and combinations thereof.

17. The wound dressing of claim 9, wherein the first anti-microbial agent comprises one or more of: PHMB, PHMB derivatives, PEHMB, silver, zinc, copper, and combinations thereof.

18. The wound dressing of claim 9, wherein the chelating agent comprises EDTA.

19. The wound dressing of claim 9, further comprising one or more of: a haemostatic agent, a protein inhibitor, a growth factor, collagen, an enzyme, an agent to induce directional bacterial growth, a means to impart bacteriacidal or bacteriostatic activity, an agent to destabilize metabolic activity, a vaso-dilator, an agent to inhibit or destroy biofilm formation, a light-activated agent, an ultrasound-activated agent, a sonication-activated agent, and combinations thereof.

20. The wound dressing of claim 9, wherein the antimicrobial agent and the chelating agent are exclusively contained in different layers of the wound dressing.

21. A wound dressing, comprising:
a first inner layer; and
second and third outer layers, wherein each of the first, second and third layers contain an anti-microbial agent and a chelating agent.

22. The wound dressing of claim 21, wherein the first inner layer is substantially hydrophilic, and the second and third outer layers are substantially hydrophobic.

23. The wound dressing of claim 22, wherein the second and third outer layers comprise a hydrophilic finish.

24. The wound dressing of claim 21, further comprising a delivery agent for containing and releasing at least one of the anti-microbial agent and the chelating agent.

25. The wound dressing of claim 24, wherein the delivery agent comprises one or more of: a hydrogel, phosphate glass, powdered starch, or a starch film.

26. The wound dressing of claim 21, wherein the one or more layers are formed, at least in part, by one or more of: natural fibers, synthetic fibers, cellulose, cotton, Rayon, Nylon, acrylic, polyester, polyurethane, polyurethane foam, hydrogels, starch, a starch film, a biodegradable material, and combinations thereof.

27. The wound dressing of claim 21, wherein the first anti-microbial agent comprises one or more of: PHMB, PHMB derivatives, PEHMB, silver, zinc, copper, and combinations thereof.

28. The wound dressing of claim 21, further comprising one or more of: a haemostatic agent, a protein inhibitor, a growth factor, collagen, an enzyme, an agent to induce directional bacterial growth, a means to impart bacteriacidal or bacteriostatic activity, an agent to destabilize metabolic activity, a vaso-dilator, an agent to inhibit or destroy biofilm formation, a light-activated agent, an ultrasound-activated agent, a sonication-activated agent, and combinations thereof.

29. A wound dressing comprising:
a first layer disposed on a first side of the dressing adapted to be applied to the wound surface, the first layer containing at least one anti-microbial agent;
a second layer adjacent to the first layer, and disposed on a side thereof opposite the first side of the dressing, the second layer containing a cell-signaling agent.

30. The wound dressing of claim 29, wherein the first layer is an outer layer and the second layer is an inner layer, of the wound dressing.

* * * * *